United States Patent
Yokoo et al.

(10) Patent No.: US 9,277,479 B2
(45) Date of Patent: Mar. 1, 2016

(54) WIRELESS COMMUNICATION SYSTEM AND WIRELESS COMMUNICATION APPARATUS

(71) Applicant: FUJITSU LIMITED, Kawasaki-shi, Kanagawa (JP)

(72) Inventors: Kaoru Yokoo, Yokosuka (JP); Yoji Ohashi, Fucyu (JP); Tatsuya Kikuzuki, Sodegaura (JP); Ichirou Ida, Yokohama (JP); Kazumi Kasai, Shibuya (JP)

(73) Assignee: FUJITSU LIMITED, Kawasaki (JP)

( * ) Notice: Subject to any disclaimer, the term of this patent is extended or adjusted under 35 U.S.C. 154(b) by 133 days.

(21) Appl. No.: 14/159,017

(22) Filed: Jan. 20, 2014

(65) Prior Publication Data

US 2014/0133290 A1    May 15, 2014

Related U.S. Application Data

(63) Continuation of application No. PCT/JP2011/067039, filed on Jul. 27, 2011.

(51) Int. Cl.
*H04W 40/14* (2009.01)
*H04W 36/30* (2009.01)
*H04L 12/00* (2006.01)
(Continued)

(52) U.S. Cl.
CPC ............ *H04W 40/14* (2013.01); *A61B 5/0028* (2013.01); *H04B 7/0802* (2013.01); *H04B 7/12* (2013.01); *H04L 1/04* (2013.01); *H04L 1/08* (2013.01); *H04L 12/00* (2013.01); *H04L 12/403* (2013.01); *H04L 45/22* (2013.01); *H04L 45/28* (2013.01); *H04W 24/00* (2013.01); *H04W 36/30* (2013.01);

(Continued)

(58) Field of Classification Search
None
See application file for complete search history.

(56) References Cited

U.S. PATENT DOCUMENTS 6,266,360 B1    7/2001    Okamoto
2004/0147289 A1    7/2004    Paljug et al.
(Continued)

FOREIGN PATENT DOCUMENTS

JP    H06-85794 A    3/1994
JP    08-84101    3/1996
(Continued)

OTHER PUBLICATIONS

JPOA—Office Action for Japanese Patent Application No. 2013-525495 issued on Sep. 16, 2014, with English translation of relevant part: p. 1 line 17 to p. 2 line 16 and p. 3 line 17 to line 27.
(Continued)

*Primary Examiner* — Gary Mui
(74) *Attorney, Agent, or Firm* — Fujitsu Patent Center

(57) ABSTRACT

A wireless communication system includes first and second wireless communication apparatuses. The first wireless communication apparatus includes a plurality of communication units that perform communication in different frequency bands. The plurality of communication units transmits the same control signal and data in the different frequency bands to keep allocation of communication slots for the second wireless communication apparatus on a plurality of paths. When detecting a communication failure while connecting to and communicating with one communication unit through one path, the second wireless communication apparatus switches to another communication unit and continues the communication through another path.

13 Claims, 13 Drawing Sheets

(51) Int. Cl.
*H04W 24/00* (2009.01)
*H04L 12/403* (2006.01)
*A61B 5/00* (2006.01)
*H04L 12/707* (2013.01)
*H04L 12/703* (2013.01)
*H04B 7/12* (2006.01)
*H04L 1/04* (2006.01)
*H04L 1/08* (2006.01)
*H04B 7/08* (2006.01)
*H04W 76/02* (2009.01)
*H04L 29/14* (2006.01)
*G06F 19/00* (2011.01)

(52) U.S. Cl.
CPC ............. *G06F 19/3418* (2013.01); *H04L 69/40* (2013.01); *H04W 76/025* (2013.01)

(56) References Cited

U.S. PATENT DOCUMENTS

| | | |
|---|---|---|
| 2005/0002421 A1 | 1/2005 | Ito et al. |
| 2005/0063486 A1 | 3/2005 | Yen et al. |
| 2007/0010256 A1 | 1/2007 | Klabunde et al. |
| 2008/0227389 A1* | 9/2008 | Sakata et al. ................ 455/39 |
| 2008/0287076 A1* | 11/2008 | Shen et al. ................ 455/114.3 |
| 2009/0010311 A1 | 1/2009 | Collier et al. |
| 2009/0275293 A1 | 11/2009 | Ida |
| 2010/0322177 A1* | 12/2010 | Luo et al. ................ 370/329 |

FOREIGN PATENT DOCUMENTS

| | | |
|---|---|---|
| JP | H08-265833 A | 10/1996 |
| JP | H09-205393 A | 8/1997 |
| JP | 2003-273799 A | 9/2003 |
| JP | 2004-7103 A | 1/2004 |
| JP | 2004-40645 A | 2/2004 |
| JP | 2010-21984 A | 1/2010 |
| JP | 2010-114774 A | 5/2010 |
| JP | 2011-976 A | 1/2011 |

OTHER PUBLICATIONS

International Search Report, mailed in connection with PCT/JP2011/067039 and mailed Aug. 30, 2011.

EESR—The Extended European Search Report issued on May 7, 2015 for corresponding European Application No. 11870026.9.

* cited by examiner

| LEVEL | DESCRIPTION |
|---|---|
| 7 | Emergency/Medical Event Report |
| 6 | High Priority medical data or network control |
| 5 | Medical data or network control |
| 4 | Voice |
| 3 | Video |
| 2 | Execellent Effort |
| 1 | Best Effort |
| 0 | Background |

FIG. 13 ically pointed out in the claims.

WIRELESS COMMUNICATION SYSTEM AND WIRELESS COMMUNICATION APPARATUS

CROSS-REFERENCE TO RELATED APPLICATION

This application is a continuation application of International Application PCT/JP2011/067039 filed on Jul. 27, 2011 which designated the U.S., the entire contents of which are incorporated herein by reference.

FIELD

The embodiment discussed herein relates to a wireless communication system and wireless communication apparatus for performing wireless communication.

BACKGROUND

In recent years, in the medical and healthcare fields, intra-body wireless communication technology has received a lot of attention, in which data obtained by a sensor attached to a human body is transmitted and received wirelessly in order to collect information on the human body with maintaining user's QoL (Quality of Life) and make use of the information for medical treatment and health maintenance.

As the intra-body wireless communication technology, a BAN (Body Area Network) has been proposed, for example. The BAN is standardized at IEEE 802.15.6, which defines physical layer (PHY) specifications including modulation methods and data rates in different frequency bands (for example, 400 MHz/900 MHz/2.4 GHz), etc.

As related art, there has been proposed a technique of sharing some components both for performing intra-body communication and for performing other communication.

Japanese Laid-open Patent Publication No. 2010-21984

Since the BAN deals with medical data, higher reliability than conventional wireless communication is needed. Therefore, there is a demand for a technique for resuming communication in a short time quickly even if a communication disconnection occurs due to a communication failure or the like.

SUMMARY

According to an aspect of the embodiments to be discussed herein, there is provided A wireless communication system including: a first wireless communication apparatus including a plurality of communication units configured to perform communication in different frequency bands; and a second wireless communication apparatus configured to connect to and communicate with the communication units, wherein: the plurality of communication units transmits a same control signal and data in the different frequency bands so as to keep allocation of communication slots for the second wireless communication apparatus on a plurality of paths; and the second wireless communication apparatus, upon detecting a communication failure while connecting to and communicating with one of the plurality of communication units through one of the plurality of paths, switches to another of the plurality of communication units and continues communication through another of the plurality of paths.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 13 illustrates data priority levels.

DESCRIPTION OF EMBODIMENTS

Figure 1:
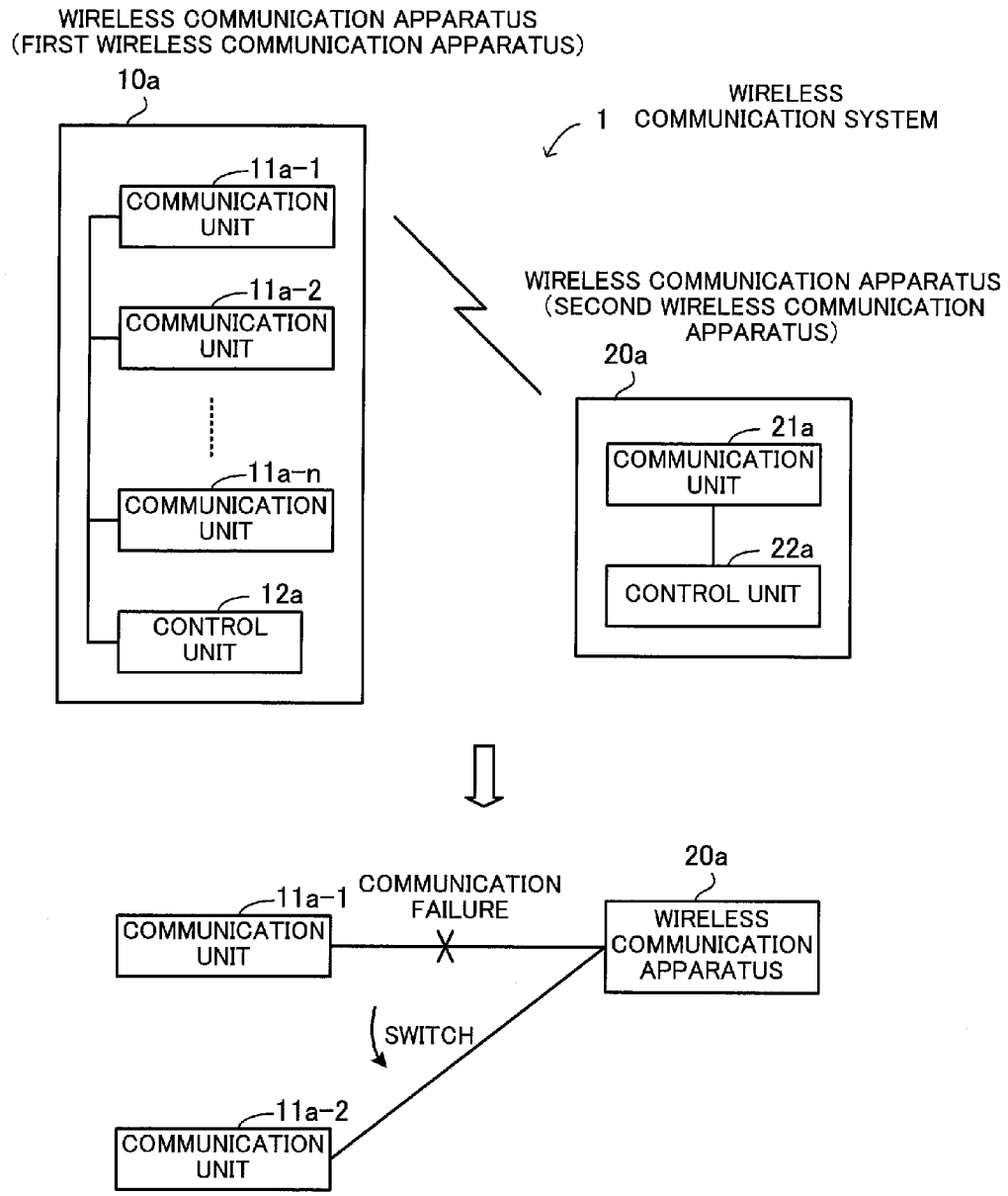
FIG. 1 illustrates an example of a configuration of a wireless communication system.

Hereinafter, an embodiment of the present invention will be described with reference to the accompanying drawings. FIG. 1 illustrates an example of a configuration of a wireless communication system. A wireless communication system 1 includes a wireless communication apparatus 10a (first wireless communication apparatus) and a wireless communication apparatus 20a (second wireless communication apparatus).

The wireless communication apparatus 10a includes communication units 11a-1 to 11a-n and a control unit 12a. The communication units 11a-1 to 11a-n are a plurality of communication interface units (PHY) that perform communication in different frequency bands. In this connection, the communication units 11a-1 to 11a-n may be configured on the same hardware. The control unit 12a controls the communication of the communication units 11a-1 to 11a-n or communication with an external network.

The wireless communication apparatus 20a includes a communication unit 21a and a control unit 22a. The communication unit 21a performs communication with any of the communication units 11a-1 to 11a-n. The control unit 22a controls the communication of the communication unit 21a and the operations of external devices and other devices.

The communication units 11a-1 to 11a-n transmit the same control signal and data in different frequency bands so as to keep allocation of communication slots for the wireless communication apparatus 20a on a plurality of paths in the different frequency bands.

The wireless communication apparatus 20a connects to and communicates with any one of the communication units 11a-1 to 11a-n. Assume that the wireless communication apparatus 20a connects to and communicates with the communication unit 11a-1 through a path. When detecting a communication failure, the wireless communication apparatus 20*a* autonomously switches to another communication unit 11*a*-2 and continues the communication through another path.

For example, when detecting a communication failure in communication with the communication unit 11*a*-1 through a path in a first frequency band (2.4 GHz), the wireless communication apparatus 20*a* switches the connection to the communication unit 11*a*-2 that uses a path in a second frequency band (900 MHz), and continues the communication with the communication unit 11*a*-2 in the second frequency band.

As described above, in the wireless communication system 1, the wireless communication apparatus 10*a* transmits the same control signal and data from the plurality of communication units 11*a*-1 to 11*a*-*n* in different frequency bands so as to keep allocation of communication slots for the wireless communication apparatus 20*a* on a plurality of paths. Then, when a communication failure occurs, the wireless communication apparatus 20*a* switches from the communication unit currently in use to another communication unit.

By doing so, any of the communication units 11*a*-1 to 11*a*-*n* becomes ready to receive communication from the wireless communication apparatus 20*a*. Even when a communication failure occurs in a path of a communication unit currently in use, the wireless communication apparatus 20*a* is able to switch to another communication unit and continue the communication through another path immediately. This makes it possible to reduce a communication disconnection time and to thereby resume the communication in a short time.

Figure 2:
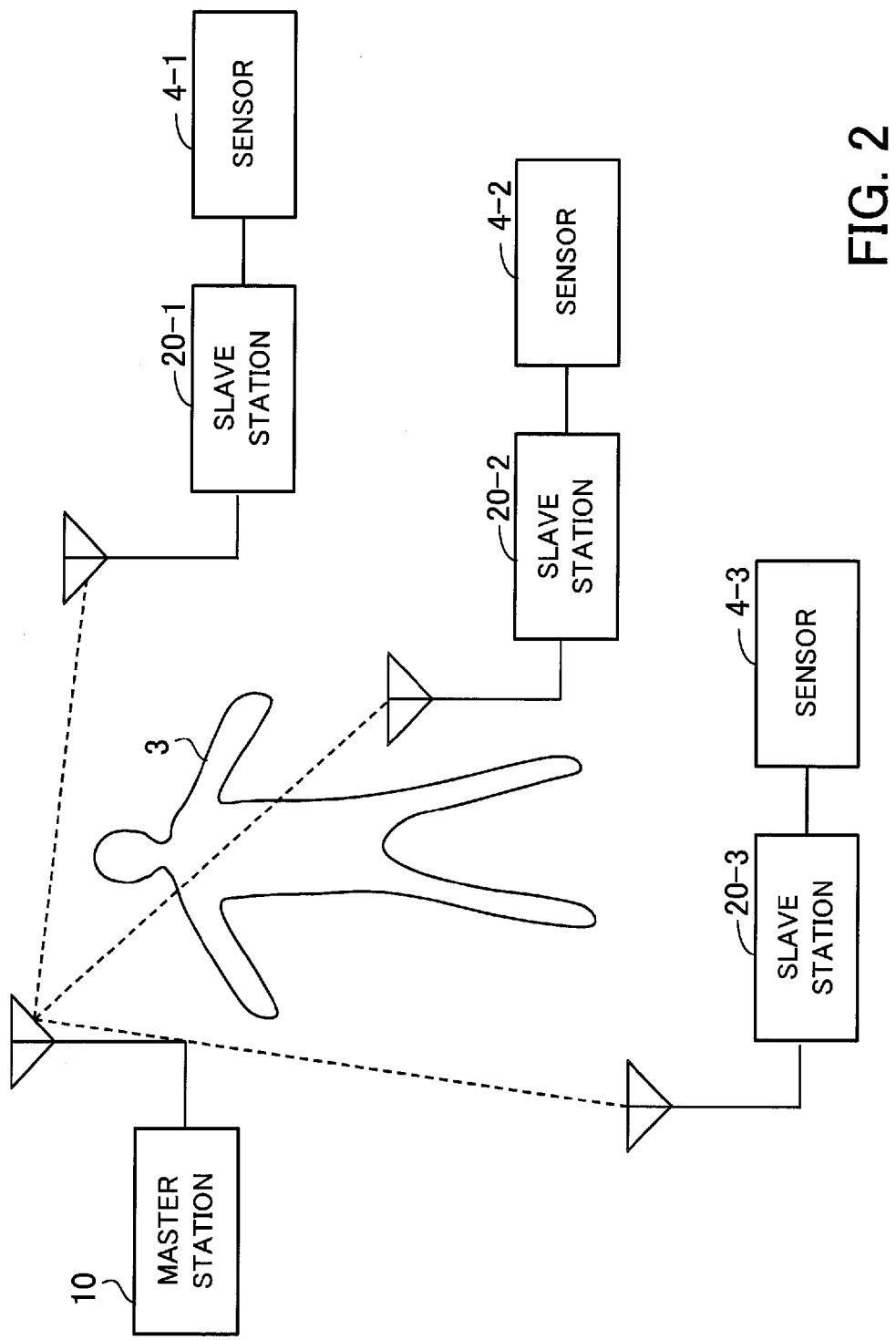
FIG. 2 illustrates an example of a configuration of a wireless communication system.

The following describes in detail the configuration and operation in the case where the wireless communication system 1 is implemented for intra-body wireless communication. FIG. 2 illustrates an example of a configuration of a wireless communication system. Sensors 4-1 to 4-3 are attached to a body 3. The sensors 4-1 to 4-3 are connected to slave stations 20-1 to 20-3, respectively. A master station 10 is located in the vicinity of the body 3. In this connection, the master station 10 corresponds to the wireless communication apparatus 10*a* of FIG. 1, and the slave stations 20-1 to 20-3 correspond to the wireless communication apparatus 20*a* of FIG. 1.

The sensors 4-1 to 4-3 are devices for measuring, for example, bio-signals such as blood pressure, pulse, blood glucose, etc. The master station 10 corresponds to, for example, a mobile telephone. The bio-signals measured by the sensors 4-1 to 4-3 are transmitted to the master station 10 via the slave stations 20-1 to 20-3.

In addition, the master station 10 is connected wirelessly to a server placed in a medical institution or the like, via a wireless base station, not illustrated, and transmits the measured bio-signals to the medical institution.

Figure 3:
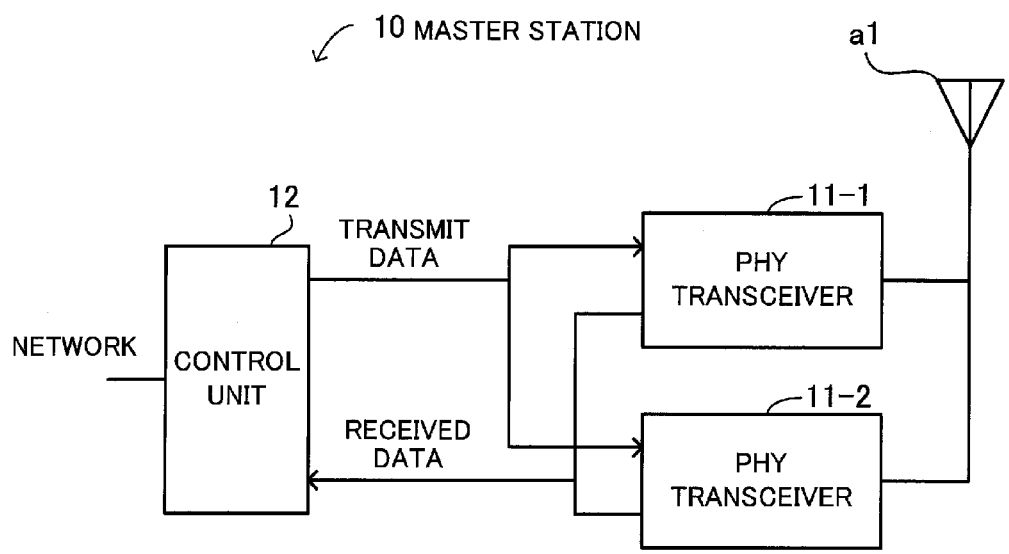
FIG. 3 illustrates an example of a configuration of a master station.

FIG. 3 illustrates an example of a configuration of a master station. The master station 10 includes an antenna a1, PHY transceivers 11-1 and 11-2, and a control unit 12. The PHY transceivers 11-1 and 11-2 correspond to the communication units 11*a*-1 and 11*a*-2 of FIG. 1, and the control unit 12 corresponds to the control unit 12*a* of FIG. 1.

The PHY transceivers 11-1 and 11-2 are transceivers that perform communication according to physical specifications including modulation methods, data rates, etc., in different frequency bands. In this connection, the PHY transceivers 11-1 and 11-2 may be configured on the same hardware. The control unit 12 controls the communication of the PHY transceivers 11-1 and 11-2 and communication with an external network.

For data transmission, the master station 10 is capable of performing data transmission from one of the PHY transceivers 11-1 and 11-2 and simultaneous data transmission from both of the PHY transceivers 11-1 and 11-2.

For data reception, the master station 10 is capable of performing data reception via one of the PHY transceivers 11-1 and 11-2 and simultaneous data reception via both of the PHY transceivers 11-1 and 11-2.

The antenna a1 is capable of operating at the frequencies of both the PHY transceivers 11-1 and 11-2. In this connection, FIG. 3 illustrates two PHY transceivers. Alternatively, three or more PHY transceivers may be installed.

Figure 4:
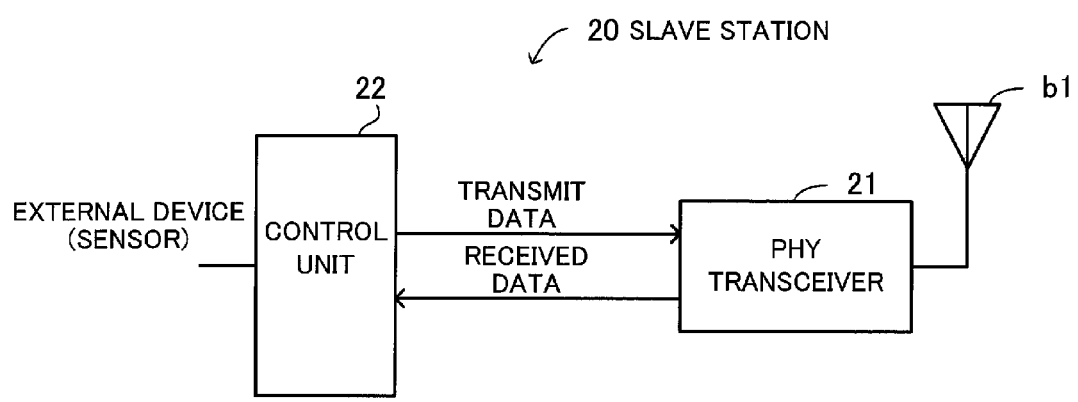
FIG. 4 illustrates an example of a configuration of a slave station.

FIG. 4 illustrates an example of a configuration of a slave station. The slave station 20 includes an antenna b1, a PHY transceiver 21, and a control unit 22. The PHY transceiver 21 corresponds to the communication unit 21*a* of FIG. 1, and the control unit 22 corresponds to the control unit 22*a* of FIG. 1.

In addition, an external device such as a sensor illustrated in FIG. 2 or the like is connected to the slave station 20 (such an external device may be built in the slave station 20). The PHY transceiver 21 performs communication with the PHY transceivers 11-1 and 11-2 of the master station 10.

The control unit 22 controls the communication of the PHY transceiver 21 and the operations of the external device. The transceiver of the slave station 20 has switching mechanism for switching between data transmission and data reception. This switching is controlled by the control unit 22.

PHY here specifies a combination of transmission frequency and transmission method at the physical layer. The PHY transceivers 11-1 and 11-2 illustrated in FIG. 3 use different frequencies. For example, the PHY transceiver 11-1 operates in 2.4 GHz band, whereas the PHY transceiver 11-2 operates in 900 MHz band.

In addition, different modulation methods and different data rates may be employed. For example, the PHY transceiver 11-1 performs π/4 shift QPSK (Quadrature phase shift keying) modulation, whereas the PHY transceiver 11-2 performs GFSK (Gaussian filtered frequency shift keying) modulation. Further, an error correction code, etc. may be set to be different.

Figure 5:
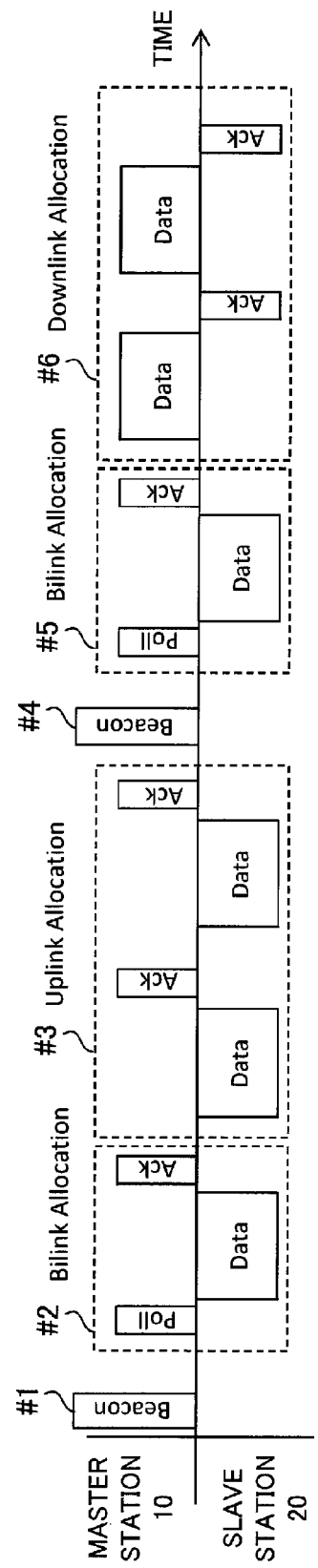
FIG. 5 illustrates a communication operation between the master station and the slave station.

The following describes operations. FIG. 5 illustrates a communication operation between a master station and a slave station. A communication state during a normal operation is depicted. In FIG. 5, Bilink Allocation (bidirectional communication allocation time) is a period of time during which the slave station 20 transmits data in response to a transmission request (polling message) from the master station 10. In this connection, during the Bilink Allocation, the master station 10 is allowed to transmit data to the slave station 20.

Uplink Allocation (uplink communication allocation time) is a period of time during which the slave station 20 transmits data to the master station 10 without polling messages. Downlink Allocation (downlink communication allocation time) is a period of time during which the master station 10 transmits data to the slave station 20.

[Beacon #1] The master station 10 transmits a beacon. When receiving the beacon, the slave station 20 recognizes which time slot is for the master station itself, based on time synchronization information included in the beacon, and establishes time synchronization with the master station 10.

[Bilink Allocation #2] The master station 10 transmits a polling message (Poll) to make a data transmission request. When receiving the polling message, the slave station 20 transmits data. The master station 10 receives the data, and returns an ACK (acknowledgement) message, which is the acknowledgement of receipt.

[Uplink Allocation #3] The slave station 20 transmits data to the master station 10. The master station 10 receives the data, and returns an ACK message.

[Beacon #4] The master station 10 transmits a beacon. The slave station 20 receives the beacon, and establishes synchronization for the next beacon interval.

[Bilink Allocation #5] The master station 10 transmits a polling message to make a data transmission request. When receiving the polling message, the slave station 20 transmits data. The master station 10 receives the data, and returns an ACK message.

[Downlink Allocation #6] The master station 10 transmits data to the slave station 20. The slave station 20 receives the data, and returns an ACK message.

Note that, in actual, communication is established to a plurality of slave stations 20 in a single beacon interval. However, for simple description, the above describes one-to-one communication between the master station 10 and the slave station 20 in a single beacon interval.

Figure 6:
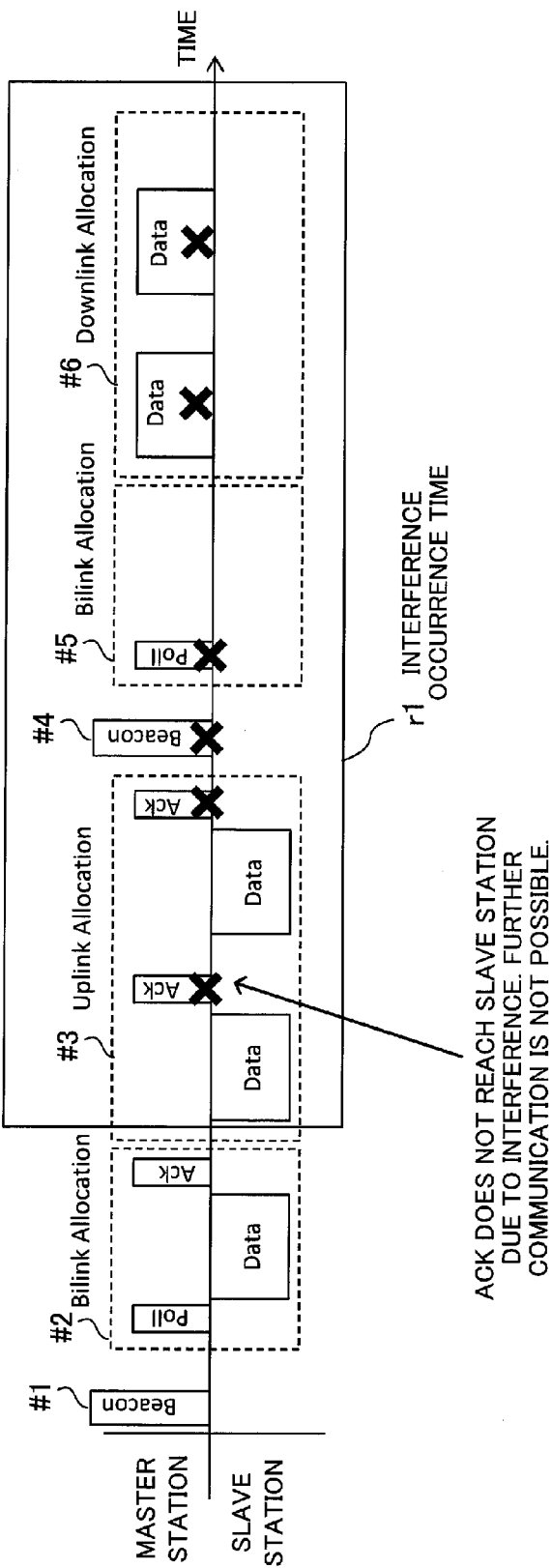
FIG. 6 illustrates a communication operation between a master station and a slave station.

The following describes how a conventional system operates in the case where a communication failure occurs. FIG. 6 illustrates a communication operation between a master station and a slave station. Assuming that interference, which causes a communication failure, occurs during the operation illustrated in FIG. 5, FIG. 6 depicts a situation where a control signal (ACK message, beacon, or the like) and data transmitted from the master station are unable to reach the slave station during an interference occurrence time r1.

The interference here is, for example, deterioration in transmission quality due to an influence of a human body and other obstacles. Or it may be interference coming from another network in the same system or from another system (including noise from a microwave (2.4 GHz)), or another.

Referring to FIG. 6, in the beginning of the Uplink Allocation #3, data transmitted from the slave station reaches the master station, but the slave station is unable to receive an ACK message due to interference caused only to the slave station.

Since the master station has received the data, the master station is unable to notice the interference immediately. Therefore, the master station keeps on transmitting beacons, polling message, and so on. However, the slave station is unable to receive them and thus to make appropriate responses.

The following describes how the wireless communication system 1 operates when interference occurs. It is assumed that one or a plurality of slave stations 20 is connected to a single master station 10, and the master station 10 transmits and receives data from a plurality of PHY transceivers (whose center frequencies differ from each other by a specified amount or greater) at the same time. The slave station 20 selects one of the plurality of PHY transceivers of the master station 10 to transmit and receive data.

In this case, the master station 10 transmits a control signal and data from the plurality of PHY transceivers at the same time so as to always keep a state where all of the PHY transceivers are ready to receive data from the slave stations 20.

The slave station 20 performs communication with a single PHY transceiver of the master station 10. When interference causes communication degradation, the slave station 20 immediately switches to another PHY transceiver of the master station 10 and continues the communication.

At this time, the master station 10 transmits the same control signal and data from all of the PHY transceivers. Therefore, the slave station 20 is able to autonomously switch the PHY transceiver without notifying the master station 10 of the switching of the PHY transceiver. This technique enables the slave station 20 to resume the communication immediately.

The following describes a specific example of the operation. In the following description, assume that the PHY transceiver 11-1 of the master station 10 and the slave station 20 perform communication in 2.4 GHz frequency band, and the PHY transceiver 11-2 of the master station 10 and the slave station 20 perform communication in 900 MHz frequency band.

Figure 7:
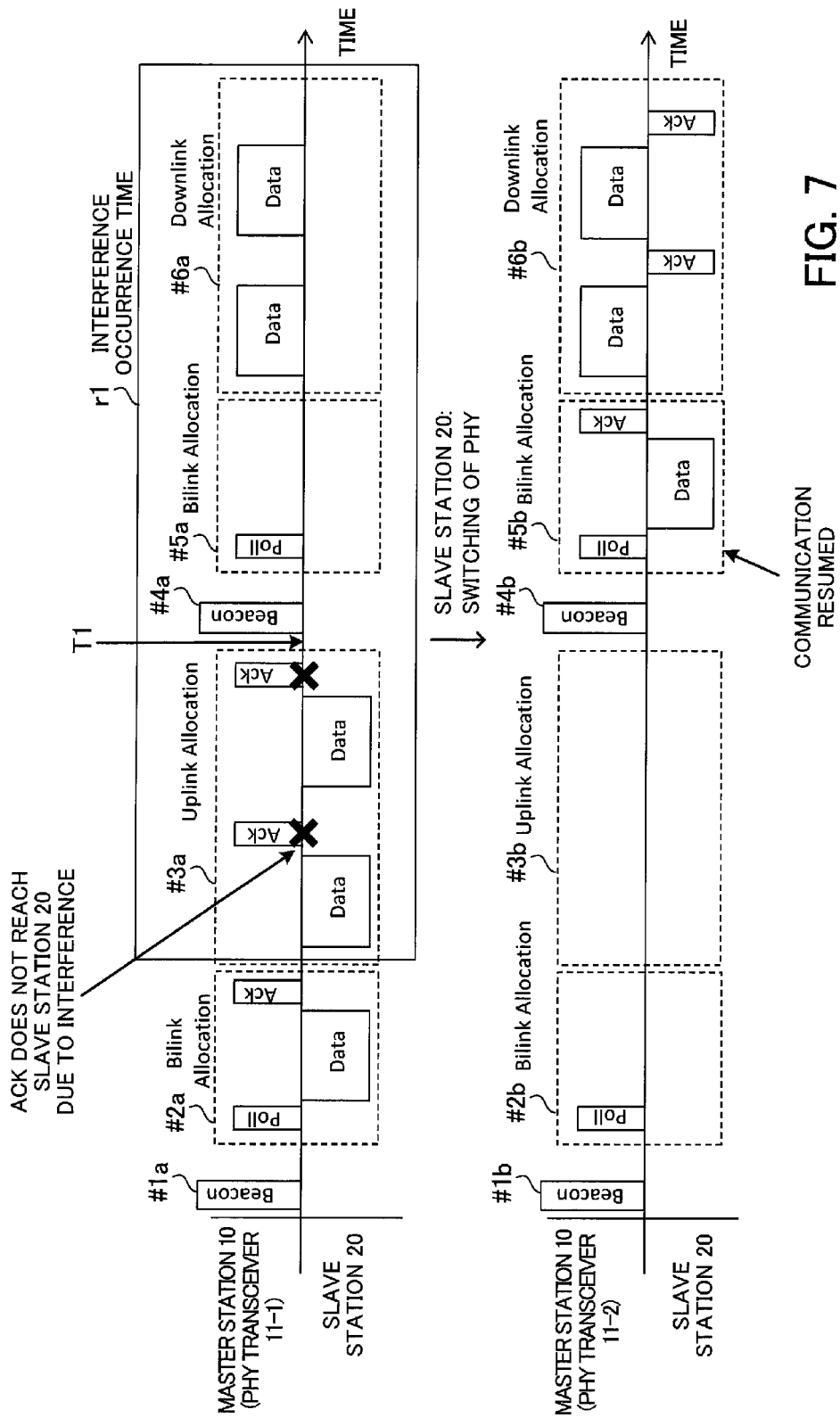
FIG. 7 illustrates a communication operation between the master station and the slave station.

FIG. 7 illustrates a communication operation between a master station and a slave station.

[Beacon #1a, #1b] The PHY transceivers 11-1 and 11-2 of the master station 10 transmit a beacon at the same time.

[Bilink Allocation #2a] The PHY transceiver 11-1 transmits a polling message to make a data transmission request. When receiving the polling message, the slave station 20 transmits data. The PHY transceiver 11-1 receives the data, and returns an ACK message.

[Bilink Allocation #2b] The PHY transceiver 11-2 transmits the polling message to make a data transmission request. However, the slave station 20 is communicating with the PHY transceiver 11-1, and therefore no further communication is performed after the transmission of the polling message in the Bilink Allocation #2b.

[Uplink Allocation #3a] The Uplink Allocation #3a is within an interference occurrence time r1. Therefore, data transmitted from the slave station 20 reaches the master station 10, but the slave station 20 is unable to receive an ACK message transmitted from the master station 10.

[Uplink Allocation #3b] Since the slave station 20 performs uplink communication with the PHY transceiver 11-1, there is no communication with the PHY transceiver 11-2 in the Uplink Allocation #3b.

[T1] The slave station 20 detects a communication failure. In this example, it is assumed that the slave station 20 determines that a failure has occurred in the communication path when the slave station 20 did not receive an ACK message twice in a row. Because of the detection of the communication failure, the slave station 20 switches from the PHY transceiver 11-1 currently in use to the other PHY transceiver 11-2.

[Beacon #4a, #4b] The PHY transceivers 11-1 and 11-2 of the master station 10 transmit a beacon at the same time.

[Bilink Allocation #5b] The PHY transceiver 11-2 transmits a polling message to make a data transmission request. When receiving the polling message, the slave station 20 transmits data. The PHY transceiver 11-2 receives the data, and returns an ACK message.

[Bilink Allocation #5a] The PHY transceiver 11-1 transmits the polling message to make a data transmission request. However, the slave station 20 is communicating with the PHY transceiver 11-2, and therefore no further communication is performed after the transmission of the polling message in the Bilink Allocation #5a.

[Downlink Allocation #6b] The PHY transceiver 11-2 transmits data to the slave station 20. The slave station 20 receives the data, and returns an ACK message.

[Downlink Allocation #6a] The PHY transceiver 11-1 transmits the data to the slave station 20. However, the slave station 20 is communicating with the PHY transceiver 11-2, and therefore there is no ACK message returned from the slave station 20 in the Downlink Allocation #6a.

Figure 8:
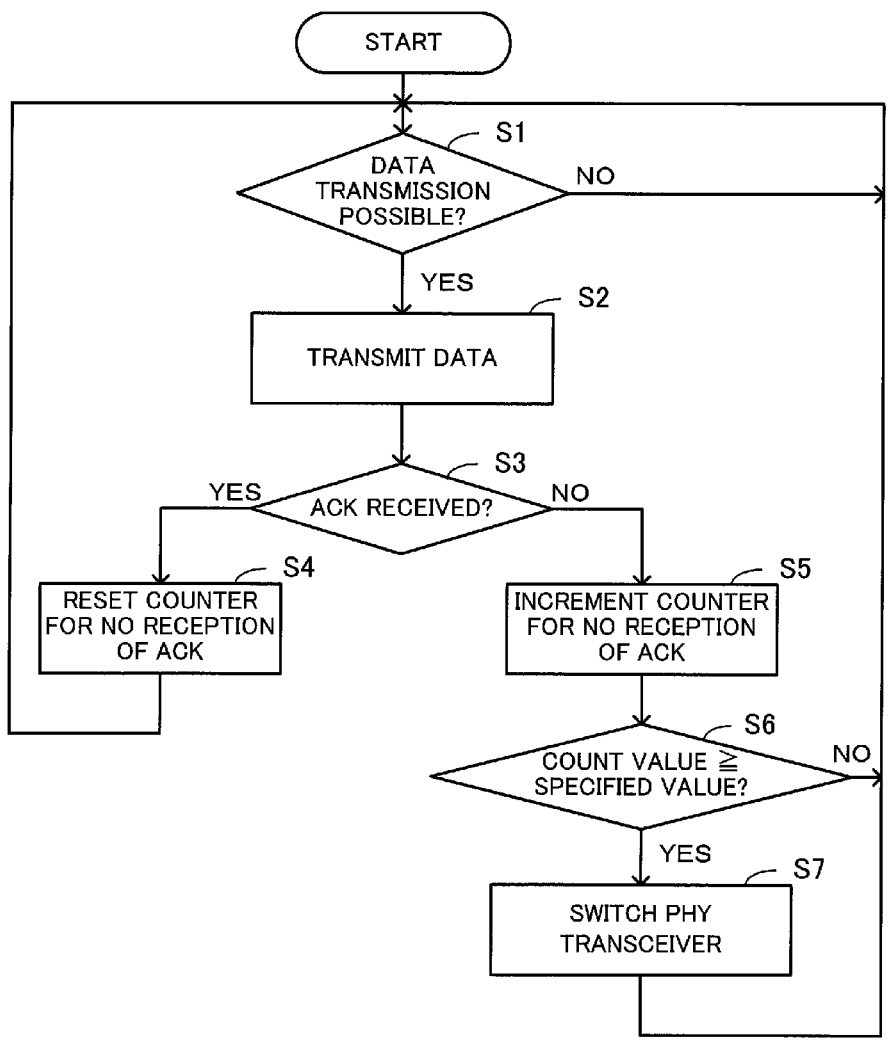
FIG. 8 is a flowchart illustrating a communication switching operation performed by the slave station.

FIG. 8 is a flowchart illustrating a communication switching operation performed by a slave station.

[S1] The control unit 22 determines whether it is possible to transmit data or not. If it is possible, the process proceeds to step S2. If it is not possible, this determination step is repeated.

[S2] The PHY transceiver 21 transmits data.

[S3] The control unit 22 determines whether there is an ACK message received or not. If an ACK message was received, the process proceeds to step S4. If an ACK message is not received, the process proceeds to step S5.

[S4] The control unit 22 resets a counter for counting how many times an ACK message was not received. Then, the process returns back to step S1.

[S5] The control unit 22 counts how many times an ACK message was not received (assume that the count value is two).

[S6] The control unit 22 determines whether the count value is greater than or equal to a specified value or not. For example, the specified value is set to two. If the count value is greater than or equal to the specified value, the process proceeds to step S7. If the control value is less than the specified value, the process returns back to step S1.

[S7] The control unit 22 switches a communication path from the PHY transceiver 11-1 to the PHY transceiver 11-2.

For example, as the timing for detecting interference by the slave station 20, the following events are considered.

(1a) An event where a control signal or data expected to be transmitted from the master station 10 was not received a specified number of times in a row, or an event where such a control signal (for example, ACK message or the like) or data was not received at a specified rate (four times out of five). Or an event where a negative acknowledgement message (NACK) was received at a specified rate or higher.

(2a) An event where a received signal, despite having a specified reception level or higher, failed to be demodulated (radio waves generated by a microwave, and a signal output from another system device fall in this case).

(3a) An event where a received signal came from another network in the same system (for example, a different master station ID (identifier) is included in place of a proper master station ID).

Detecting the above events (1a) to (3a) enables the slave station 20 to promptly recognize occurrence of a communication failure.

As described above, the master station 10 transmits a control signal such as a beacon, polling message, or the like and data from both of the PHY transceivers 11-1 and 11-2 at the same time.

At this time, in the process for detecting a communication failure, the slave station 20 determines that some failure has occurred in a communication path when, for example, the slave station 20 did not receive an ACK message twice in a row. Then, the slave station 20 switches from the PHY transceiver 11-1 currently in use to the other PHY transceiver 11-2.

Since the master station 10 transmits the same control signal and data from the PHY transceivers 11-1 and 11-2 at the same time, the master station 10 is able to continue the communication immediately even if the slave station 20 switches to the PHY transceiver 11-2. This makes it possible to reduce a communication disconnection time and to thereby resume the communication in a short time.

In this connection, after that, the slave station 20 maintains the communication with the PHY transceiver 11-2. In addition, for the case where the slave station 20 may perform the switching again, the master station 10 transmits the same control signal and data from the PHY transceiver 11-1 as well.

The following describes another operation that is performed when interference has occurred. During the normal operation, the master station 10 forms a network with one of a plurality of PHY transceivers. When the PHY transceiver currently in use experiences a communication failure, the master station 10 transmits a control signal and data from another PHY transceiver as well at the same time so as to be ready to continue the communication with the slave station 20 after the slave station 20 switches the PHY transceiver.

On the other hand, when the communication deteriorates due to interference or the like while the slave station 20 communicates with one PHY transceiver of the master station 10, the slave station 20 immediately switches to another PHY transceiver of the master station 10 and continues the communication through another path.

Figure 9:
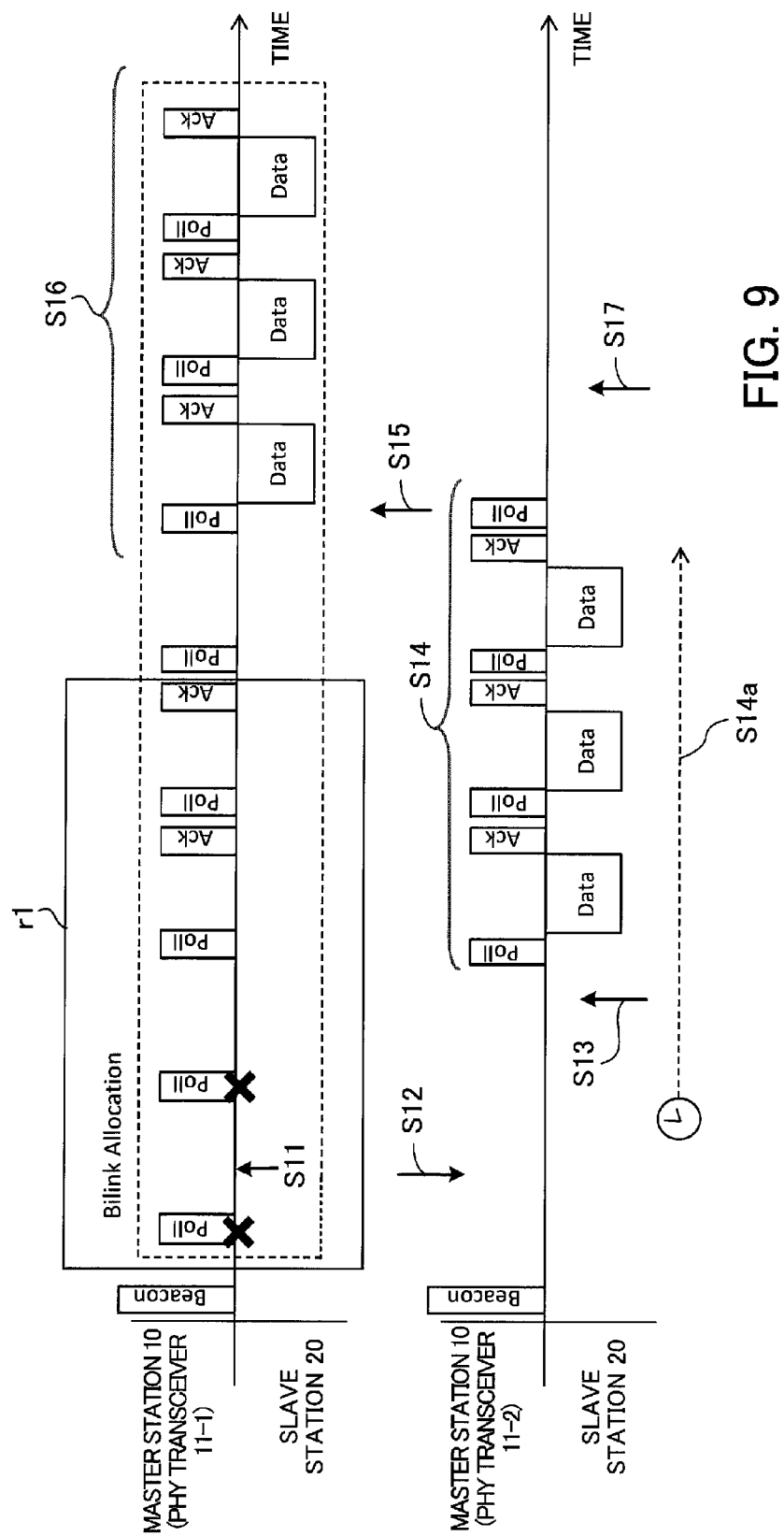
FIG. 9 illustrates a communication operation between the master station and the slave station.

The following describes a specific example of the operation. FIG. 9 illustrates a communication operation between a master station and a slave station. Bands allocated to the slave station 20 are all in Bilink Application.

[S11] While communicating with the PHY transceiver 11-1, the slave station 20 determines that interference has occurred because the slave station 20 is unable to receive polling messages, despite it is in the Bilink Allocation.

[S12] The slave station 20 switches to the PHY transceiver 11-2. At this time, the master station 10 has not activated the PHY transceiver 11-2.

[S13] The master station 10 determines that there was no data returned as a response to a polling message a specified number of times (in this example, twice in a row), and activates the PHY transceiver 11-2, so that the PHY transceivers 11-1 and 11-2 operate simultaneously.

[S14] The slave station 20 performs the communication with the PHY transceiver 11-2.

[S14a] The slave station 20 starts a timer, and maintains the communication with the PHY transceiver 11-2 for a specified period of time.

[S15] When the time is up, the slave station 20 switches to the PHY transceiver 11-1.

[S16] If it is possible to perform the communication with the PHY transceiver 11-1, the slave station 20 continues the communication with the PHY transceiver 11-1.

[S17] When recognizing that the slave station 20 has cut off the communication with the PHY transceiver 11-2, the master station 10 deactivates the PHY transceiver 11-2 (in this connection, although there is the single slave station in this example, a condition for deactivating the PHY transceiver 11-2 is that all slave stations have cut off communication with the PHY transceiver 11-2).

Figure 10:
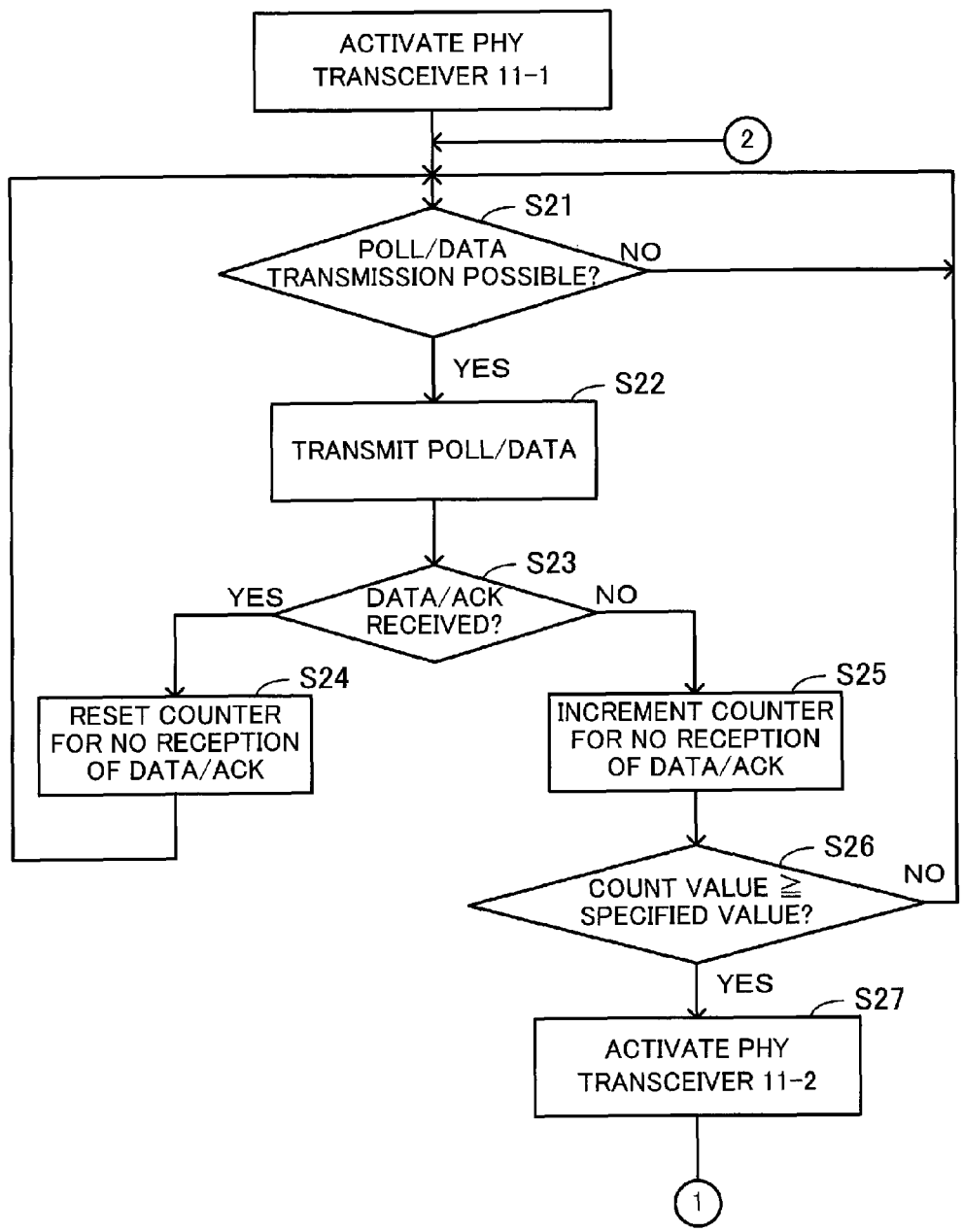
FIG. 10 is a flowchart illustrating an activation switching operation for a PHY transceiver in the master station.
Figure 11:
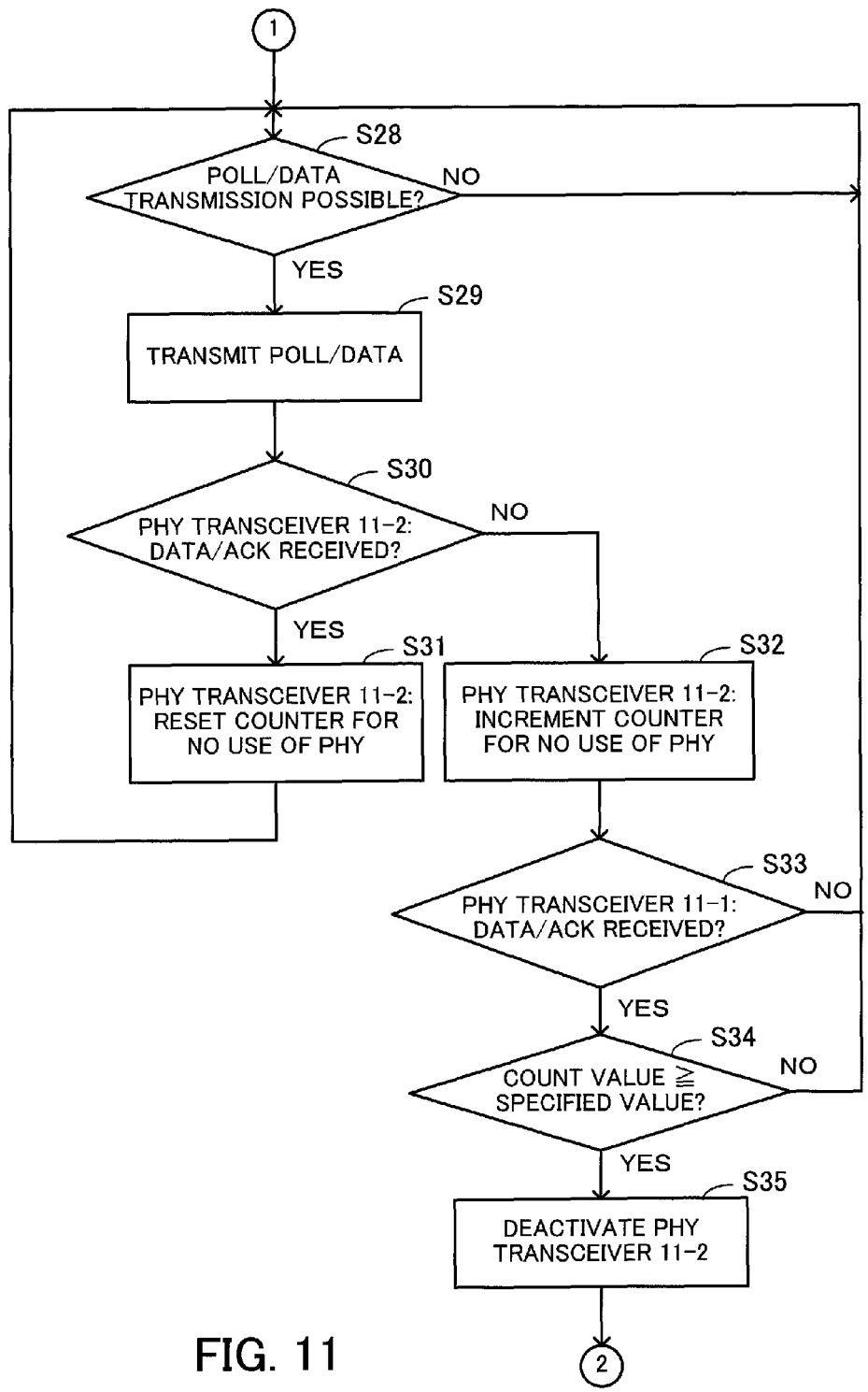
FIG. 11 is a flowchart illustrating the activation switching operation for the PHY transceiver in the master station.

FIGS. 10 and 11 are flowcharts illustrating an activation switching operation for a PHY transceiver in a master station.

[S20] The control unit 12 of the master station 10 activates the PHY transceiver 11-1.

[S21] The control unit 12 determines whether it is possible to transmit a polling message or data from the PHY transceiver 11-1 or not. If it is possible, the process proceeds to step S22. If it is not possible, this determination step is repeated.

[S22] The PHY transceiver 11-1 transmits a polling message or data.

[S23] The control unit 12 determines whether there was data received from the slave station 20 as a response to the polling message or not or whether there was an ACK message received from the slave station 20 as a response to the data or not. If there was such data or ACK message received, the process proceeds to step S24. If there was no such data or ACK message received, the process proceeds to step S25.

[S24] The control unit 12 resets a counter for counting how many times data was not received and counting how many times an ACK message was not received. Then, the process returns back to step S21.

[S25] The control unit 12 counts how many times data or ACK message was not received (it is now assumed that the count value is two).

[S26] The control unit 12 determines whether the count value is greater than or equal to a specified value or not. For example, the specified value is set to two. If the count value is greater than or equal to the specified value, the process proceeds to step S27. If the count value is less than the specified value, the process returns back to step S21.

[S27] The control unit 12 activates the PHY transceiver 11-2, so that the PHY transceivers 11-1 and 11-2 operate simultaneously.

[S28] The control unit 12 determines whether it is possible to transmit a polling message or data from the PHY transceiver 11-2 or not. If it is possible, the process proceeds to step S29. If it is not possible, this determination step is repeated.

[S29] The PHY transceiver 11-2 transmits a polling message or data.

[S30] The control unit 12 determines whether data was received at the PHY transceiver 11-2 from the slave station 20 as a response to the polling message or not or whether an ACK message was received at the PHY transceiver 11-2 from the slave station 20 as a response to the data or not. If such data or ACK message was received, the process proceeds to step S31. If such data or ACK message was not received, the process proceeds to step S32.

[S31] The control unit 12 resets the counter for counting how many times data was not received and how many times an ACK message was not received at the PHY transceiver 11-2. That is to say, in the case where the communication is performed between the PHY transceiver 11-2 and the slave station 20, the control unit 12 resets the counter. Then, the process returns back to step S28.

[S32] The control unit 12 counts how many times data or ACK message was not received at the PHY transceiver 11-2 (it is now assumed that the count value is two). That is to say, in the case where the communication is not performed between the PHY transceiver 11-2 and the slave station 20, the control unit 12 increments the count value.

[S33] The control unit 12 determines whether data was received at the PHY transceiver 11-1 from the slave station 20 as a response to the polling message or not or whether an ACK message was received at the PHY transceiver 11-1 from the slave station 20 as a response to the data or not. If such data or ACK message was received, the process proceeds to step S34. If such data or ACK message was not received, the process returns back to step S28.

[S34] The control unit 12 determines whether the count value obtained at step S32 is greater than or equal to a specified value or not. For example, the specified value is set to two. If the count value is greater than or equal to the specified value, the process proceeds to step S35. If the count value is less than the specified value, the process returns back to step S28.

[S35] The control unit 12 determines that there is no slave station 20 that is communicating with the PHY transceiver 11-2, and then deactivates the PHY transceiver 11-2. Then, the process returns back to step S21.

In this connection, in the above description, after confirming that the slave station 20 has cut off the communication with the PHY transceiver 11-2 and is served by the PHY transceiver 11-1, the control unit 12 deactivates the PHY transceiver 11-2. Alternatively, the PHY transceiver 11-2 may be deactivated before the slave station 20 is served by the PHY transceiver 11-1.

For example, as the timing for detecting interference in the master station 10, the following events are considered.

(1b) An event where a control signal or data expected to be transmitted from the slave station 20 was not received a specified number of times in a row, or an event where such a control signal (for example, ACK message or the like) or data was not received at a specified rate (four times out of five). Or an event where a negative acknowledgement message (NACK) was received at a specified rate or higher.

(2b) An event where a received signal, despite having a specified reception level or higher, failed to be demodulated (radio waves generated by a microwave, and a signal output from another system device fall in this case).

(3b) An event where a received signal came from another network in the same system (for example, a different slave station ID (identifier) is included in place of a proper slave station ID).

Detecting the above events (1b) to (3b) enables the master station 10 to promptly recognize occurrence of a communication failure.

As described above, when a communication failure has occurred while communication is performed between the PHY transceiver 11-1 and the slave station 20, the master station 10 activates the PHY transceiver 11-2 and the slave station 20 switches from the PHY transceiver 11-1 to the PHY transceiver 11-2, so as to continue the communication. With this, it becomes possible to reduce a communication disconnection time and to thereby resume the communication in a short time even when a communication disconnection occurs due to a communication failure.

Further, the master station 10 usually does not activate a plurality of PHY transceivers, and when communication switching is to be performed, activates a previously-designated PHY transceiver. This reduces power consumption and realizes efficient use of resources.

Still further, when the slave station 20 performs communication at, for example, 900 MHz for a specified period of time after switching to the PHY transceiver 11-2, the slave station 20 makes an attempt to switch to the PHY transceiver 11-1 that was used previously.

If a communication failure has been cleared, the slave station 20 continues the communication with the previous PHY transceiver 11-1 at, for example, 2.4 GHz. Then, after confirming that the slave station 20 has cut off the communication with the PHY transceiver 11-2, the master station 10 deactivates the PHY transceiver 11-2. This control makes it possible to realize efficient use of resources.

Figure 12:
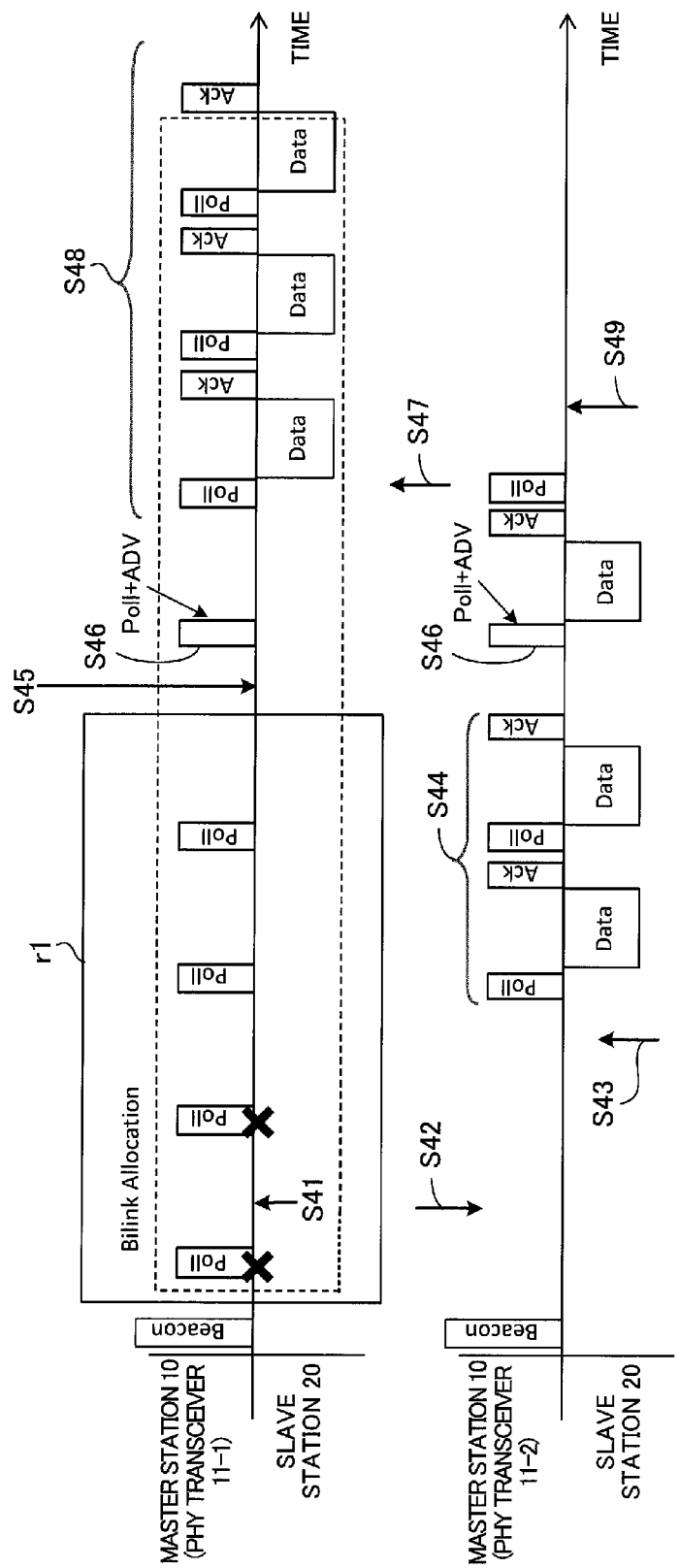
FIG. 12 illustrates a communication operation between the master station and the slave station.

The following describes the case where the master station 10 promotes the slave station 20 to switch to a previous communication source by notifying the slave station 20 that a communication failure (interference source) has been cleared. FIG. 12 illustrates a communication operation between a master station and a slave station. Bands allocated to the slave station 20 are all in Bilink Allocation.

[S41] While communicating with the PHY transceiver 11-1, the slave station 20 determines that interference has occurred because the slave station 20 is unable to receive polling messages, despite it is in the Bilink Allocation.

[S42] The slave station 20 switches to the PHY transceiver 11-2. At this time, the master station 10 has not activated the PHY transceiver 11-2.

[S43] The master station 10 determines that there was no data returned as a response to a polling message a specified number of times (in this example, twice in a row), and then activates the PHY transceiver 11-2, so that the PHY transceivers 11-1 and 11-2 operate simultaneously.

[S44] The slave station 20 performs the communication with the PHY transceiver 11-2.

[S45] The master station 10 detects that the interference source has been cleared.

[S46] The master station 10 notifies the slave station 20 communicating with the PHY transceiver 11-2 that the interference caused to the PHY transceiver 11-1 has been cleared. For example, the master station 10 transmits a polling message (Poll) and an interference source clearance message (ADV) together.

[S47] The slave station 20 switches the communication destination from the PHY transceiver 11-2 to the PHY transceiver 11-1.

[S48] The slave station 20 continues the communication with the PHY transceiver 11-1.

[S49] After confirming that all slave stations 20 have cut off the communication with the PHY transceiver 11-2, the master station 10 deactivates the PHY transceiver 11-2.

As described above, when the master station 10 determines that a communication failure in the PHY transceiver 11-1 has been cleared, the master station 10 notifies the slave station 20 of the clearance.

When receiving the message, the slave station 20, which has been communicating with the PHY transceiver 11-2, switches to the PHY transceiver 11-1. Then, after confirming that the slave station 20 has cut off the communication with the PHY transceiver 11-2, the master station 10 deactivates the PHY transceiver 11-2. The above technique makes it possible to realize efficient use of resources.

The following describes a modification example. In this modification example, an operation of switching between an operation mode (hereinafter, referred to as operation mode A) described with reference to FIG. 7 and an operation mode (hereinafter, referred to as operation mode B) described with reference to FIG. 9 under a switching condition is controlled. The first describes the case of switching an operation mode based on data traffic priority, which is used as the switching condition.

FIG. 13 illustrates data priority levels. In the BAN, data priority levels (user priority) are defined from level 0 to level 7 as MAC (Media Access Control) levels. The level 7 is the highest priority level, i.e., for Emergency/Medical Event Report, and is used in an emergency case for medical purpose.

During the normal operation, the master station 10 operates in the operation mode B, and when traffic for level 7 has been generated or when a ratio of traffic for level 6 has reached a specified value, i.e., when a switching condition is satisfied, switches to the operation mode A to increase QoS (Quality of Service).

More specifically, the master station 10 operates in the operation mode B during the normal operation, and when detecting a communication failure in the communication between the PHY transceiver 11-1 and the slave station 20, activates the PHY transceiver 11-2, and transmits the same control signal and data as the PHY transceiver 11-1, from the PHY transceiver 11-2, thereby allocating communication slots for the slave station 20.

Then, when traffic for level 7 has been generated or when a ratio of traffic for level 6 has reached the specified value while the master station 10 is in the operation mode B, the master station 10 transmits the same control signal and data from both the PHY transceivers 11-1 and 11-2 in different frequency bands, to move to the operation mode A in which allocation of the communication slots for the slave station 20 are always kept.

With the above technique, the master station operates in the operation mode B at the time of communication of normal bio-signals, which reduces power consumption and realizes efficient use of resources. Then, when an emergency bio-signal is to be communicated, the operation mode is switched to the operation mode A. Even if a communication disconnection occurs, the communication is resumed with another PHY transceiver immediately, which enhances reliability.

When there exists no traffic for level 7 and a ratio of traffic for level 6 becomes lower than the specified value, on the contrary, the operation mode is switched from the operation mode A to the operation mode B.

As another switching condition, the operation mode may be switched according to desired power consumption. Assume that there is another operation mode C in which only a single PHY transceiver is used.

In the case where low power consumption is prioritized, the master station 10 is set to operate in the operation mode C. In the case where power consumption and QoS are balanced, the master station 10 is set to operate in the operation mode B. In the case where QoS is prioritized, the master station 10 is set to operate in the operation mode A. The operation mode switching may be performed according to an instruction from the control unit 12 or may automatically be performed according to a remaining battery level.

As described above, in the wireless communication system 1, the slave station 20, which is a terminal side, is able to autonomously switch a PHY transceiver without a complicated procedure. Therefore, even if a communication disconnection has occurred, it is possible to reduce the communication disconnection time and to thereby resume the communication in a short time.

In this connection, the above description uses two PHY transceivers. Alternatively, three or more PHY transceivers may be used. In this case, the master station 10 may transmit a control signal and data from all of the PHY transceivers at the same time, or a rule as to which PHY transceiver to use may be determined in advance between the master station 10 and the slave station 20. In addition, in the case of using three or more PHY transceivers, a rule as to in what order the slave station makes an attempt to perform communication may be determined in advance.

It becomes possible to reduce a communication disconnection time and to thereby resume the communication in a short time.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that various changes, substitutions, and alterations could be made hereto without departing from the spirit and scope of the invention.

What is claimed is:
1. A wireless communication system comprising:
a first wireless communication apparatus including a plurality of communicators which perform communication in different frequency bands; and
a second wireless communication apparatus configured to connect to and communicate with the communicators,
wherein:
the plurality of communicators transmits a same control signal and data in the different frequency bands so as to keep allocation of communication slots for the second wireless communication apparatus on a plurality of paths;

the second wireless communication apparatus receives a first beacon included in the control signal, establishes time synchronization with a first communication slot based on the first beacon transmitted from the first wireless communication apparatus, and communicates with a first communicator in the first communication slot; and the second wireless communication apparatus, upon detecting a communication failure while connecting to and communicating with the first communicator, establishes time synchronization with a second communicator based on a second beacon included in the control signal transmitted from the first wireless communication apparatus, and switches to the second communicator and continues communication through a second communication slot.

2. The wireless communication system according to claim 1, wherein the second wireless communication apparatus determines that the communication failure has occurred when the second wireless communication apparatus did not receive a signal expected to be transmitted from the first wireless communication apparatus, a certain number of times in a row or at a certain rate or higher, or when the second wireless communication apparatus received a negative acknowledgement message at a certain rate or higher.

3. The wireless communication system according to claim 1, wherein the second wireless communication apparatus determines that the communication failure has occurred when a received signal, despite having a certain electric field strength or higher, failed to be demodulated.

4. The wireless communication system according to claim 1, wherein the second wireless communication apparatus determines that the communication failure has occurred when a received signal came from another network in a same system.

5. The wireless communication system according to claim 1, wherein, when the second wireless communication apparatus performs the communication through said another path for a certain period of time after switching to said another communicator, the second wireless communication apparatus makes an attempt to switch to the one communicator used previously.

6. A wireless communication apparatus comprising:
a plurality of communicators which perform communication in different frequency bands; and
a controller which controls the communication, wherein:
the plurality of communicators transmits a same control signal and data in the different frequency bands so as to keep allocation of communication slots for a peer apparatus on a plurality of paths;
the peer apparatus receives a first beacon included in the control signal, establishes time synchronization with a first communication slot based on the first beacon transmitted from the wireless communication apparatus, and communicates with a first communicator in the first communication slot; and
the peer apparatus, upon detecting a communication failure while connecting to and communicating with the first communicator, establishes time synchronization with a second communicator based on a second beacon included in the control signal transmitted from the wireless communication apparatus, and switches to the second communicator and continues communication through a second communication slot.

7. A wireless communication apparatus comprising:
a communicator which connects to and communicates with a peer communicator of a peer apparatus that includes a plurality of peer communicators which perform communication in different frequency bands; and
a controller which controls the communication, wherein:
the plurality of peer communicators transmits a same control signal and data in the different frequency bands so as to keep allocation of communication slots for the wireless communication apparatus on a plurality of paths;
the communicator receives a first beacon included in the control signal, establishes time synchronization with a first communication slot based on the first beacon transmitted from the peer apparatus, and communicates with a first peer communicator in the first communication slot; and
the controller, upon detecting a communication failure while communication is performed through one of the plurality of paths by connecting to and communicating with the first peer communicator, establishes time synchronization with a second peer communicator based on a second beacon included in the control signal transmitted from the peer apparatus, and switches to the second peer communicator and continues communication through a second communication slot.

8. A wireless communication system comprising:
a first wireless communication apparatus including a plurality of communicators which perform communication transmitting a same control signal and data in different frequency bands and a controller for controlling the communication; and
a second wireless communication apparatus configured to connect to and communicate with the communicators, wherein:
the second wireless communication apparatus receives a first beacon included in the control signal, establishes time synchronization with a first communication slot based on the first beacon transmitted from the first wireless communication apparatus, and communicates with a first communicator in the first communication slot; and
the controller, upon detecting a communication failure while communicating with the first communicators, activates a second communicator, and transmits a same control signal and data as the first communicator, from the second communicator so as to allocate communication slots for the second wireless communication apparatus; and
the second wireless communication apparatus, upon detecting the communication failure, establishes time synchronization with a second communicator based on a second beacon included in the control signal transmitted from the first wireless communication apparatus, and switches to the second communicator and continues the communication through a second path.

9. The wireless communication system according to claim 8, wherein the controller determines that the communication failure has occurred when a signal expected to be transmitted from the second wireless communication apparatus was not received, a certain number of times in a row or at a certain rate or higher, or when a negative acknowledgement message was received at a certain rate or higher.

10. The wireless communication system according to claim 8, wherein the controller determines that the communication failure has occurred when a received signal, despite having a certain electric field strength or higher, failed to be demodulated.

11. The wireless communication system according to claim 8, wherein the controller determines that the communication failure has occurred when a received signal came from another network in a same system.

12. The wireless communication system according to claim 8, wherein, when the second wireless communication apparatus performs the communication through the second path for a certain period of time after switching to the second communicator, the second wireless communication apparatus makes an attempt to switch to the first communicator used previously.

13. The wireless communication system according to claim 8, wherein
- the controller, upon determining that the communication failure in the first communicator has been cleared, sends the second wireless communication apparatus a message indicating that the communication failure has been cleared,
- the second wireless communication apparatus, upon receiving the message, switches to the first communicator, and
- the controller deactivates the second communicator after confirming that the second wireless communication apparatus has cut off the communication with the second communicator.

\* \* \* \* \*